(12) United States Patent  
Awdeh

(10) Patent No.: US 10,254,528 B2  
(45) Date of Patent: Apr. 9, 2019

(54) MICROSCOPE INSERT

(71) Applicant: Richard Awdeh, Miami, FL (US)

(72) Inventor: Richard Awdeh, Miami, FL (US)

(73) Assignee: Nanophthalmos, LLC, Miami, FL (US)

( * ) Notice: Subject to any disclaimer, the term of this patent is extended or adjusted under 35 U.S.C. 154(b) by 70 days.

(21) Appl. No.: 15/123,041

(22) PCT Filed: Mar. 13, 2015

(86) PCT No.: PCT/US2015/020584  
§ 371 (c)(1),  
(2) Date: Sep. 1, 2016

(87) PCT Pub. No.: WO2015/138988  
PCT Pub. Date: Sep. 17, 2015

(65) Prior Publication Data  
US 2017/0075100 A1  Mar. 16, 2017

Related U.S. Application Data

(60) Provisional application No. 61/952,793, filed on Mar. 13, 2014.

(51) Int. Cl.  
*G02B 21/36* (2006.01)  
*G02B 21/22* (2006.01)  
(Continued)

(52) U.S. Cl.  
CPC .......... *G02B 21/365* (2013.01); *A61B 3/0025* (2013.01); *A61B 3/0041* (2013.01);  
(Continued)

(58) Field of Classification Search  
CPC .. G02B 21/365; G02B 21/18; G02B 27/0101; G02B 27/286; G02B 21/362;  
(Continued)

(56) References Cited

U.S. PATENT DOCUMENTS 5,359,417 A   10/1994  Muller et al.  
7,800,820 B2   9/2010  Awdeh  
(Continued)

FOREIGN PATENT DOCUMENTS

EP   1235094 A2   8/2002  
EP   2184005 A1   5/2010  
(Continued)

OTHER PUBLICATIONS

International Search Report from the U.S. Patent and Trademark Office for International Application No. PCT/US2015/020584 dated Jun. 24, 2015.

(Continued)

*Primary Examiner* — Jack Dinh  
(74) *Attorney, Agent, or Firm* — Finnegan, Henderson, Farabow, Garrett & Dunner LLP

(57) ABSTRACT

A microscope insert includes a beam splitter, a camera, a processing unit, a display device, and a polarizer element. The beam splitter is configured to direct a first portion of first light from an object in a first direction and a second portion of the first light in a second direction. The display device is configured to generate a graphical representation of information relevant to the object and transmit second light corresponding to the graphical representation. The polarizer element is configured to modify a polarization of the second light from the display device. The beam splitter directs a first portion of the modified second light in the first direction to a viewing device. The first portion of the modified second light and the first portion of the first light from the object are combined for simultaneous viewing of the graphical representation and the object by the user.

16 Claims, 12 Drawing Sheets

(51) Int. Cl.
*G02B 21/00* (2006.01)
*G02B 27/28* (2006.01)
*A61B 3/00* (2006.01)
*A61B 3/13* (2006.01)
*A61B 3/14* (2006.01)
*G02B 21/18* (2006.01)
*G02B 27/01* (2006.01)

(52) U.S. Cl.
CPC ............... *A61B 3/13* (2013.01); *A61B 3/14* (2013.01); *G02B 21/0012* (2013.01); *G02B 21/18* (2013.01); *G02B 21/22* (2013.01); *G02B 21/361* (2013.01); *G02B 21/362* (2013.01); *G02B 21/368* (2013.01); *G02B 27/0101* (2013.01); *G02B 27/283* (2013.01); *G02B 27/286* (2013.01); *G02B 2027/0141* (2013.01)

(58) Field of Classification Search
CPC ............ G02B 27/283; G02B 21/0012; G02B 21/368; G02B 21/22; A61B 3/14; A61B 3/13; A61B 3/0025; A61B 3/0041
See application file for complete search history.

(56) References Cited

U.S. PATENT DOCUMENTS

| | | |
|---|---|---|
| 2003/0223037 A1 | 12/2003 | Chernyak |
| 2006/0247659 A1 | 11/2006 | Moeller et al. |
| 2008/0291532 A1 | 11/2008 | Xu et al. |
| 2009/0093798 A1 | 4/2009 | Charles |
| 2011/0019151 A1 | 1/2011 | Schuhrke et al. |
| 2011/0122365 A1 | 5/2011 | Kraus et al. |
| 2011/0292340 A1 | 12/2011 | Shimizu et al. |
| 2012/0197102 A1 | 8/2012 | Hanebuchi et al. |
| 2012/0330129 A1 | 12/2012 | Awdeh |
| 2013/0088414 A1 | 4/2013 | Artsyukhovich et al. |
| 2013/0271845 A1 | 10/2013 | Butler et al. |

FOREIGN PATENT DOCUMENTS

| | | |
|---|---|---|
| EP | 2322083 A1 | 5/2011 |
| EP | 102014201571 A1 | 7/2015 |
| WO | WO2009/029638 | 3/2009 |

OTHER PUBLICATIONS

Written Opinion from the U.S. Patent and Trademark Office for International Application No. PCT/US2015/020584 dated Jun. 24, 2015.

European Search Report, dated Jun. 7, 2017, in the European Application No. EP14845155.2, filed on Nov. 4, 2016 by Awdeh.

European Search Report, dated Sep. 19, 2017, in the European Application No. EP15761534.5, filed on Apr. 28, 2017 by Awdeh.

European Search Report, dated Oct. 19. 2017, in the European Application No. EP15760909.0, filed on Apr. 28, 2017 by Awdeh.

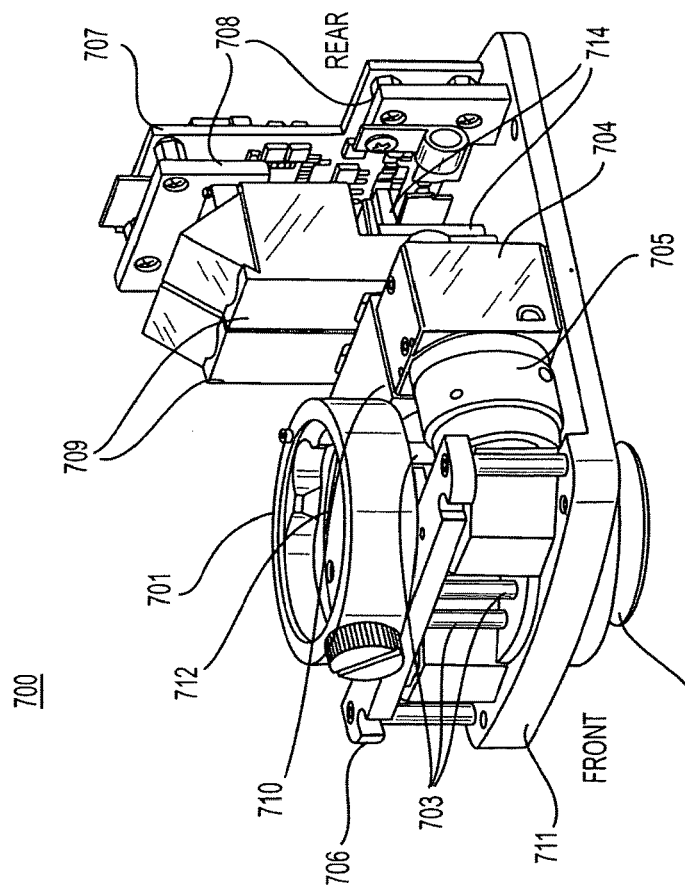
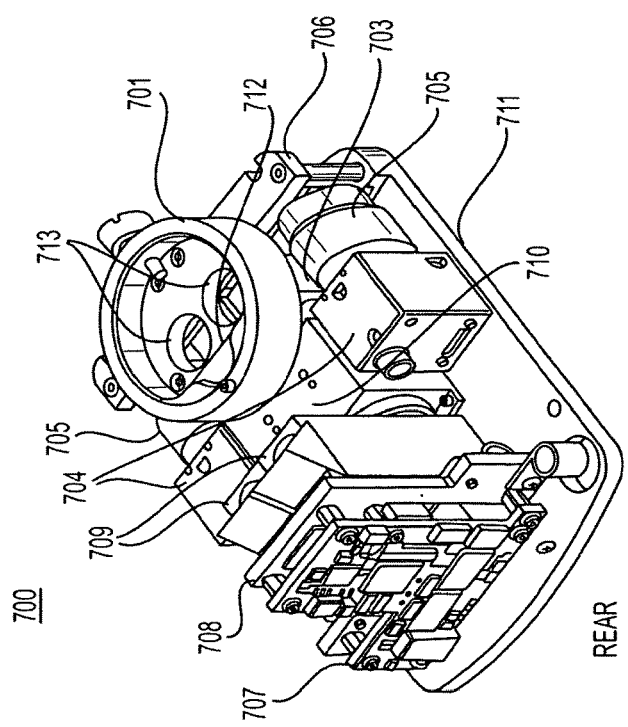
FIG. 7B
FIG. 7A

MICROSCOPE INSERT

CROSS REFERENCE TO RELATED APPLICATIONS

This application claims the benefit of priority to U.S. Provisional Application No. 61/952,793, filed Mar. 13, 2014.

TECHNICAL FIELD

This disclosure is related in general to surgical microscopes and in particular to a microscope insert for surgical microscopes.

BACKGROUND

Surgery carried out through a microscope, such as the cataract surgery, presents special challenges for the surgeon and the microscope. Not only must each procedure and step be carried out accurately, but parameters of the surgery and biological data of the patient must be monitored closely to achieve desired results and ensure safety of the patient. Existing surgical systems, such as ophthalmology microscopes, do not have the ability to display the surgical site and related data within the same field of view. As a result, the surgeon must move away from the eye pieces of the microscope to an external display device in order to view the related data and then move back to the eye pieces in order to continue the surgery. This is not only inconvenient, but may also cause patient safety issues. In addition, existing surgical systems do not provide sufficient prompts or guidance to the surgeon to ensure a correct procedure is carried out. It is desired to provide system-generated prompts for the surgeon during the surgery.

SUMMARY

According to an embodiment, a microscope insert includes a beam splitter configured to receive first light from an object. The beam splitter directs a first portion of the first light in a first direction to a viewing device and directs a second portion of the first light in a second direction. The microscope insert further includes a camera configured to receive the second portion of the first light from the beam splitter and to generate a first signal representing the object, and a processing unit configured to receive the first signal representing the object and determine characteristics of the object by analyzing the first signal. The processing unit further generates a second signal representing information relevant to the object. The microscope insert further includes a display device configured to receive the second signal from the processing unit and generate a graphical representation of the information based on the second signal and transmit second light corresponding to the graphical representation. The microscope insert further includes a polarizer element configured to modify a polarization of the second light from the display device. The beam splitter receives the modified second light from the polarizer element and directs a first portion of the modified second light in the first direction to the viewing device. The first portion of the modified second light and the first portion of the first light from the object are combined for simultaneous viewing of the graphical representation and the object by the user.

According to another embodiment, a microscope insert includes a first channel, a second channel, and a processing unit. The first and second channels each include a beam splitter configured to receive first light from an object. The beam splitter directs a first portion of the first light in a first direction to a viewing device and directs a second portion of the first light to a second direction. The first and second channels each further include a camera configured to receive the second portion of the first light from the beam splitter and generate a first signal representing the object, a display device, and a polarizer element. The processing unit is configured to receive the first signal representing the object, determine characteristics of the object by analyzing the first signal, and generate a second signal representing information relevant to the object. The display device is configured to receive the second signal from the processing unit, generate a graphical representation of the information based on the second signal, and transmit second light representing the graphical representation. The polarizer element is configured to modify a polarization of the second light from the display device. The beam splitter receives the modified second light from the polarizer element and directs a first portion of the modified second light in the first direction, alone with the first portion of the first light from the object, to the viewing device for simultaneous viewing of the graphical representation and the object by the user.

According to another embodiment, a method for generating an overlaid image in a microscope includes receiving first light from an object, directing a first portion of the first light in a first direction to a viewing device and a second portion of the first light in a second direction to a camera, generating, based on the second portion of the first light, a graphical representation of information relevant to the object, projecting second light corresponding to the graphical representation, modifying a polarization of the second light, and directing at least a portion of the modified second light in the first direction so that the portion of the modified second light and the first portion of the first light are combined for simultaneously viewing of the object and the graphical representation by a user.

According to another embodiment, a method for generating an overlaid image in a microscope includes receiving a first light from a microscope corresponding to a first image corresponding to an object, directing a first portion of the first light to a viewing device and a second portion of the first light to a camera, generating, based on the second portion of the first light, a second image to be overlaid on the first mage, projecting second light corresponding to the second image, directing a first portion of the second light to the camera and a second portion of the second light to the viewing device, and combining the first portion of the first light and the second portion of the second light to form a combined image. The combined image includes the first image corresponding to the object and the second image generated by the display device. The second image is rendered over the first image.

BRIEF DESCRIPTION OF THE DRAWINGS

FIGS. 7A and 7B are perspective views of a microscope insert having various components installed therein according to an embodiment;

DESCRIPTION OF THE EMBODIMENTS

Reference will now be made in detail to exemplary embodiments of the disclosure, examples of which are illustrated in the accompanying drawings. Wherever possible, the same reference numbers will be used throughout the drawings to refer to the same or like parts.

Figure 1:
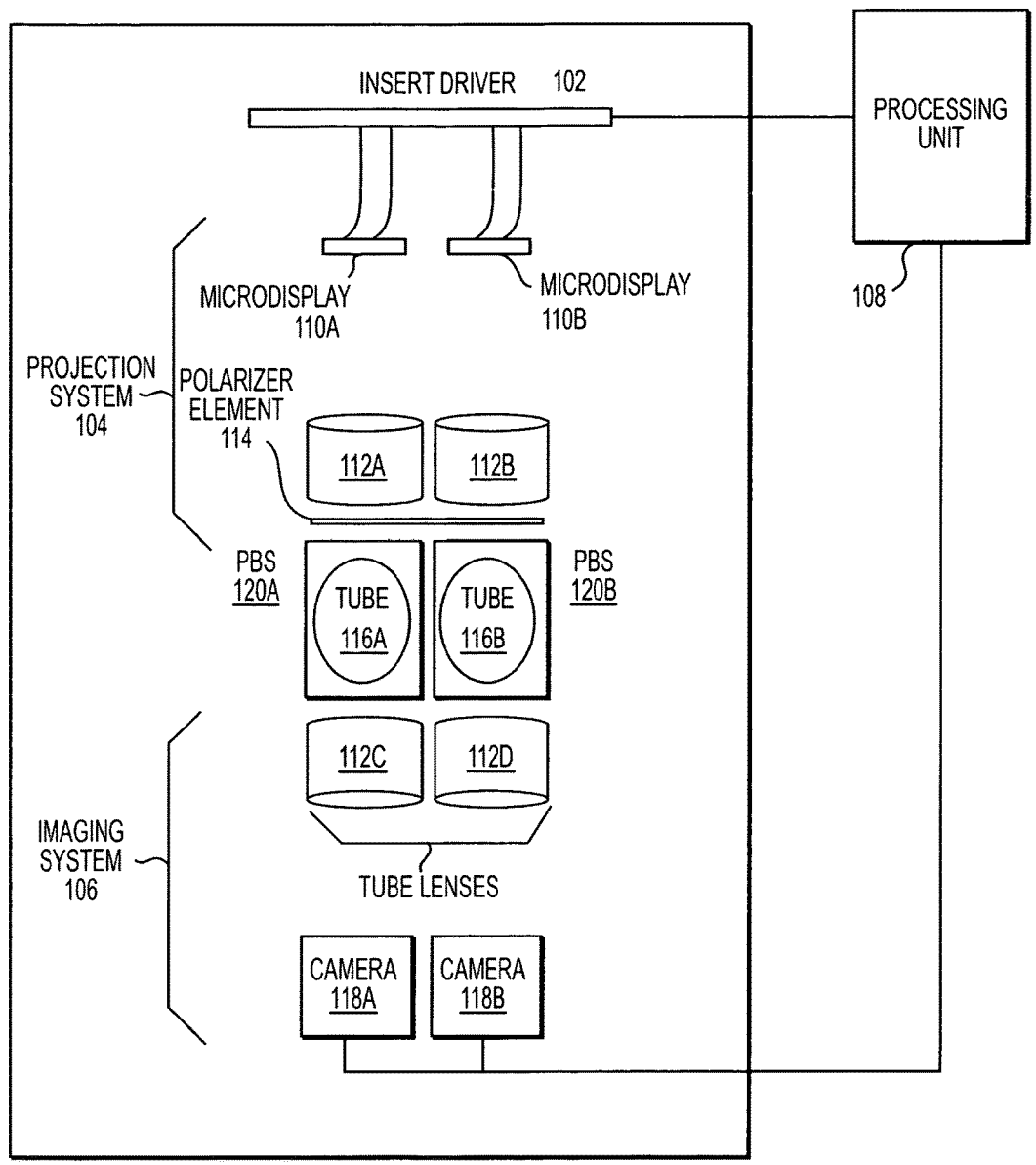
FIG. 1 is a schematic diagram of a microscope insert according to an embodiment.

As shown in FIG. 1, a microscope insert 100 includes a projection system 104 and an imaging system 106. Projection system 104 includes one or more display devices 110A and 110B and one or more sets of tube lenses 112A and 112B for projecting images from the display devices 110A and 110B. Imaging system 106 includes one or more cameras 118A and 118B and one or more sets of tube lenses 112C and 112D for focusing images to cameras 118A and 118B. Microscope insert 100 further includes one or more polarizing beam splitters (PBS) 120A and 120B, which will be further described below.

The above components of insert 100 form individual optical channels that generate respective images for left and right eyes of a user. Each optical channel includes a display device 110A/110B, a camera 118A/118B, a polarizing beam splitter 120A/120B, and corresponding tube lenses 112A/112B and 112C/112D. In a further embodiment, a polarizer element 114 may be disposed between tube lenses 112A/112B and polarizing beam splitters 120A/120B. Alternatively, polarizer element 114 may include different pieces for respective optical channels.

Although FIG. 1 shows two optical channels for microscope insert 100, one of ordinary skill in the art would recognize that insert 100 may have any number of optical channels, each having a structure similar to those depicted in FIG. 1. When microscope 100 includes two or more optical channels, videos/images generated by the optical channels are configured so as to provide a user with stereoscopic rendering.

In an embodiment, cameras 118A and 118B are digital imaging devices, such as the Point Grey FL3-U3-13S2C-CS manufactured by Point Grey Research. However, a number of different cameras may be used, providing different features, such as a CMOS or CCD based sensor, a global or rolling shutter, and a range of resolutions at about 20 FPS or higher.

In an embodiment, display devices 110A and 110B may be LCOS (Liquid Crystal on Silicon) microdisplay devices, each of which has pixels that can be individually adjusted to match or exceed the brightness of the microscope. Other display technologies may also be used, such as OLED, DLP, T-OLED, MEMS, and LCD-based displays.

Insert 100 also includes a display driver circuit 102 to control display devices 110A and 110B and/or other system elements or features. Display driver circuit 102 may generate video/image data that are suitable for rendering by display devices 110A and 110B.

Insert 100 is connected to a processing unit 108 via standard communication protocols. Processing unit 108 may or may not be disposed within insert 100. Processing unit 108 receives video/image signals from cameras 118A and 118B and sends the video/image signals to driver circuit 102 for rendering the videos/images on display devices 110A and 110B. Processing unit 108 may apply additional processing on videos/images data received from cameras 118A and 118B. For example, processing unit 108 may perform image processing techniques, such as image registration, pattern recognition, image filtering, image enhancement, and the like.

Processing unit 108 may also be connected to other peripherals to collect data to be used by microscope insert 100, to generate visual guidance for navigation during a surgical procedure, or to provide alternative graphical user interfaces on external display devices to supplement the display through microscope insert 100.

Figure 2:
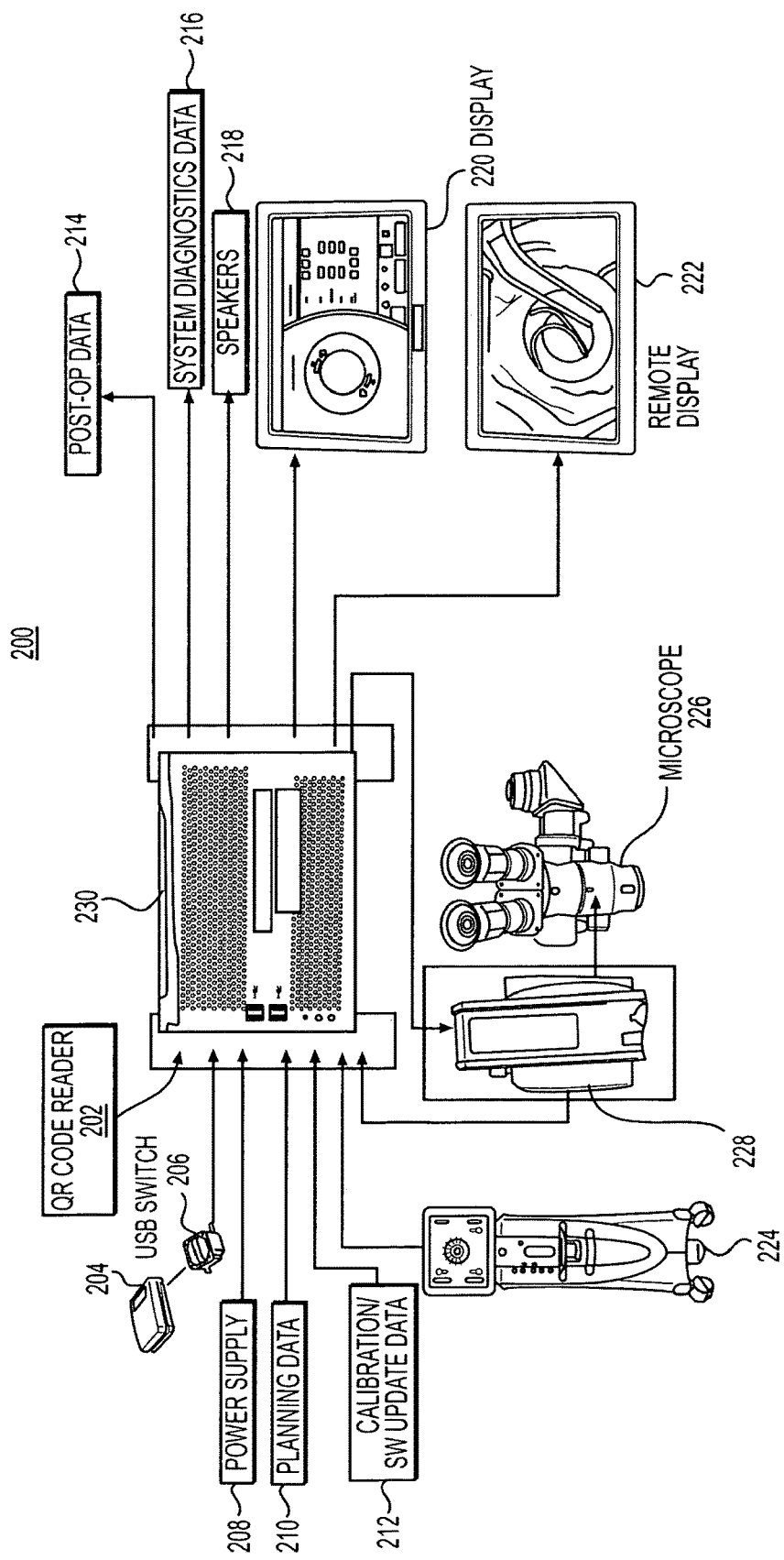
FIG. 2 illustrates a surgical system including the microscope insert according to an embodiment.

FIG. 2 illustrates a surgical system 200 including a microscope insert 228 according to a further embodiment. Surgical system 200 includes a microscope 226 coupled to microscope insert 228. Microscope insert 228 generally corresponds to microscope insert 100 of FIG. 1. Insert 228 communicates with a processing unit 230, which corresponds to processing unit 108 of FIG. 1.

Microscope 226 receives light or optical signals reflected from an object through its lens system and the polarized beam splitters (e.g., PBS's 120A and 120B), which pass the optical signals to the cameras (e.g., cameras 118A and 118B) of microscope insert 228. The cameras of microscope insert 228 convert the optical signals to digital data representing videos/images of the object and transmit the digital data to processing unit 230.

Processing unit 230 performs image processing on the digital data and sends processed data and relevant commands to the driver circuit (e.g., driver circuit 102) of microscope 226. Based on the processed data and the commands from the driver circuit, display devices (e.g., display devices 110A and 110B) of microscope insert 228 generate optical signals representing processed videos/images of the object and project the optical signals to polarized beam splitters 120A and 120B. Polarized beam splitters 120A and 120B pass the optical signals to the eye pieces of microscope 226 for viewing by a user. The driver circuit may also control, for example, the brightness or contrast of display devices 110A and 110B.

Processing unit 230 may also communicate with additional input devices, such as a QR code reader 202, a foot pedal 204, a USB switch 206, a power supply 208, and one or more external storage devices providing surgical planning data 210 or calibration and software update data 212. Additionally, processing unit 230 may be further connected to a surgical support system 224 that is suitable for the underlying surgery. For example, surgical support system 224 may be the Stellaris system manufactured by Bausch & Lomb Incorporated and suitable for ophthalmic procedures. Surgical support system 224 may collect the demographical and biological data of a patient and provides the data to processing unit 230.

Still additionally, system 200 may include various output devices, such as speakers 218, an external display device 220, and a remote display device 222. External display device 220 and remote display device 222 may be high-resolution monitors that provide additional monitoring capability outside of insert 228. Display devices 220 and 222 may be located in the same operating room as microscope 226 or at a remote location. System 200 may further include one or more storage media for storing post-operation data 214 and system diagnostics data 216. Similarly, other system components shown in FIG. 2 may also be located in different locations and connected to processing unit 230 through, for example, Ethernet, Internet, USB connections, Bluetooth connections, infrared connections, cellular connections, Wi-Fi connections, and the like.

Figure 3:
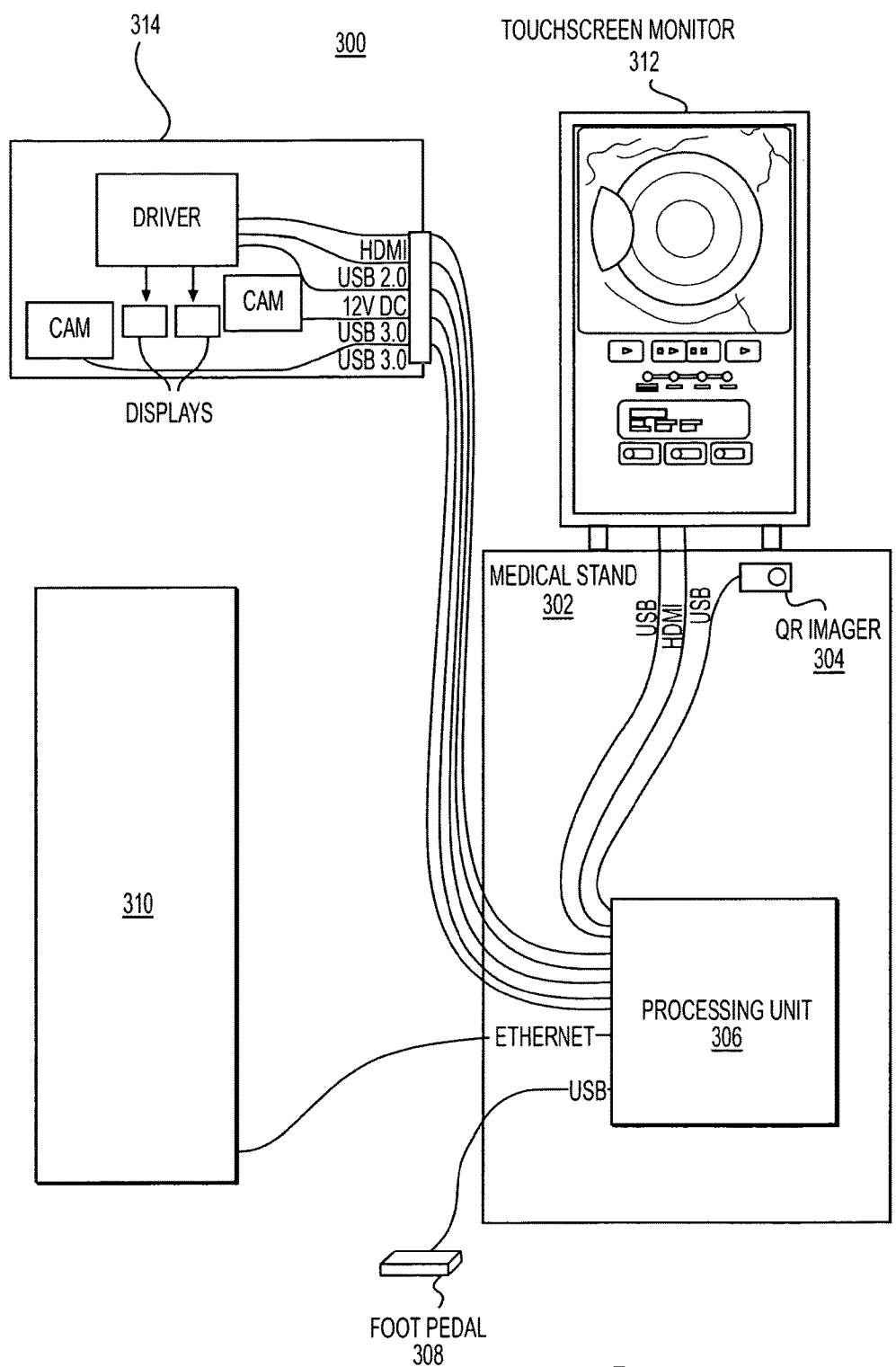
FIG. 3 illustrates electronic connections between the microscope insert and an external computer system according to an embodiment.

FIG. 3 illustrates a surgical system 300 including a microscope insert 314 according to an alternative embodiment. Microscope insert 314 generally corresponds to microscope insert 100 of FIG. 1 and is configured to generate stereoscopic images as described herein. For example, insert 314 may include two imaging cameras, two display devices, a driver circuit, and other imaging and projection optics for left and right eyes of a user.

System 300 further includes a medical stand 302, an external monitor 312, a foot pedal 308, and a surgical support system 310. Medical stand 302 may include a QR image scanner 304 configured to scan QR codes to provide information encoded in the codes. Medical stand 302 also includes a processing unit 306, which generally corresponds to processing unit 108 of FIG. 1. Processing unit 306 may be included a motherboard with interfaces, such as USB 2.0, USB 3.0, Ethernet, etc. Processing unit 306 may include a central processing unit (CPU) with heat sinks, a RAM, a video card, a power supply, a webcam, etc. Processing unit 306 is connected to other system components through its communication interfaces, such as USB ports, Ethernet ports, Internet ports, HDMI interfaces, etc. For example, processing unit 306 may be connected to microscope insert 314 and external monitor 312 through HDMI interfaces to provide high resolution video/image data to the driver circuit of insert 314 and monitor 312. Alternatively, processing unit 306 may also be connected to insert 314 and monitor 312 through USB ports to provide video/image data and control signals. Processing unit 306 may be connected to the camera of insert 314 through USB ports to receive video/image data from the camera.

Foot pedal 308 and other user input devices may be connected to processing unit 306 through one or more USB ports. Foot pedal 308 may be operated by a user to provide user input during a surgery. For example, when the user presses foot pedal 308, foot pedal 308 may generate an electronic signal. Upon receiving the electronic signal from foot pedal 308, processing unit 306 may control insert 314 accordingly.

For example, when the user presses foot pedal 308, processing unit 306 may control insert 314 to change the videos/images generated by the display devices of insert 314. With each pressing of foot pedal 308, insert 314 may toggle between two sets of videos/images. Alternatively, insert 314 may cycle through a series of videos/images when foot pedal 308 is pressed. Still alternatively, pedal 308 may have a position sensor that generates a position signal indicating a position of pedal 308 when the user partially presses pedal 308. Upon receiving the position signal from pedal 308, processing unit 306 may determine the current position of pedal 308 and control insert 314 accordingly. Processing unit 308 may control insert 314 to generate a different set of videos/images corresponding to each position of pedal 308. For example, when the user presses pedal 308 to a first position, processing unit 306 controls insert 314 to generate a first set of videos/images. When the user presses pedal 308 to a second position, processing unit 306 controls insert 314 to generate a second set of videos/images.

Surgical support system 310 may include an external data source and other surgical systems, such as a Bausch & Lomb Stellaris surgical system. Surgical support system 310 may include biological sensors that collect biological or physiological data of the patient, including, for example, heart rate, blood pressure, electrocardiogram, etc. Surgical support system 310 may further include a database that stores information of the patient, including the patient's medical history and healthcare record. The database may also include information of the underlying surgical procedure such as pre-operation analysis and planning performed by a physician, data collecting during the surgical procedure, and additional procedures recommended for post-operation follow-ups. The database may also include information of the operating physician including his or her identification, association, qualification, etc. Surgical support system 310 may be further connected to additional medical devices (not shown) such as an ultrasound imager, a magnetic resonance imaging device, a computed tomography device, etc., to collect additional image data of the patient.

Processing unit 306 may receive the information and data from surgical support system 310 and controls insert 314 to generate images based on the information and data. For example, processing unit 306 may transmit the additional image data (i.e., ultrasound data, MRI data, CT data, etc.) received from system 310 to the driver circuit of insert 314 and control the driver circuit of insert 314 to render the additional image, through the display devices, along with the microscopic images of the patient provided by the microscope. Processing unit 306 may also generate additional image data representing the biological or physiological data collected from the patient and control insert 314 to render the additional image data through the display devices of insert 314.

Figure 4:
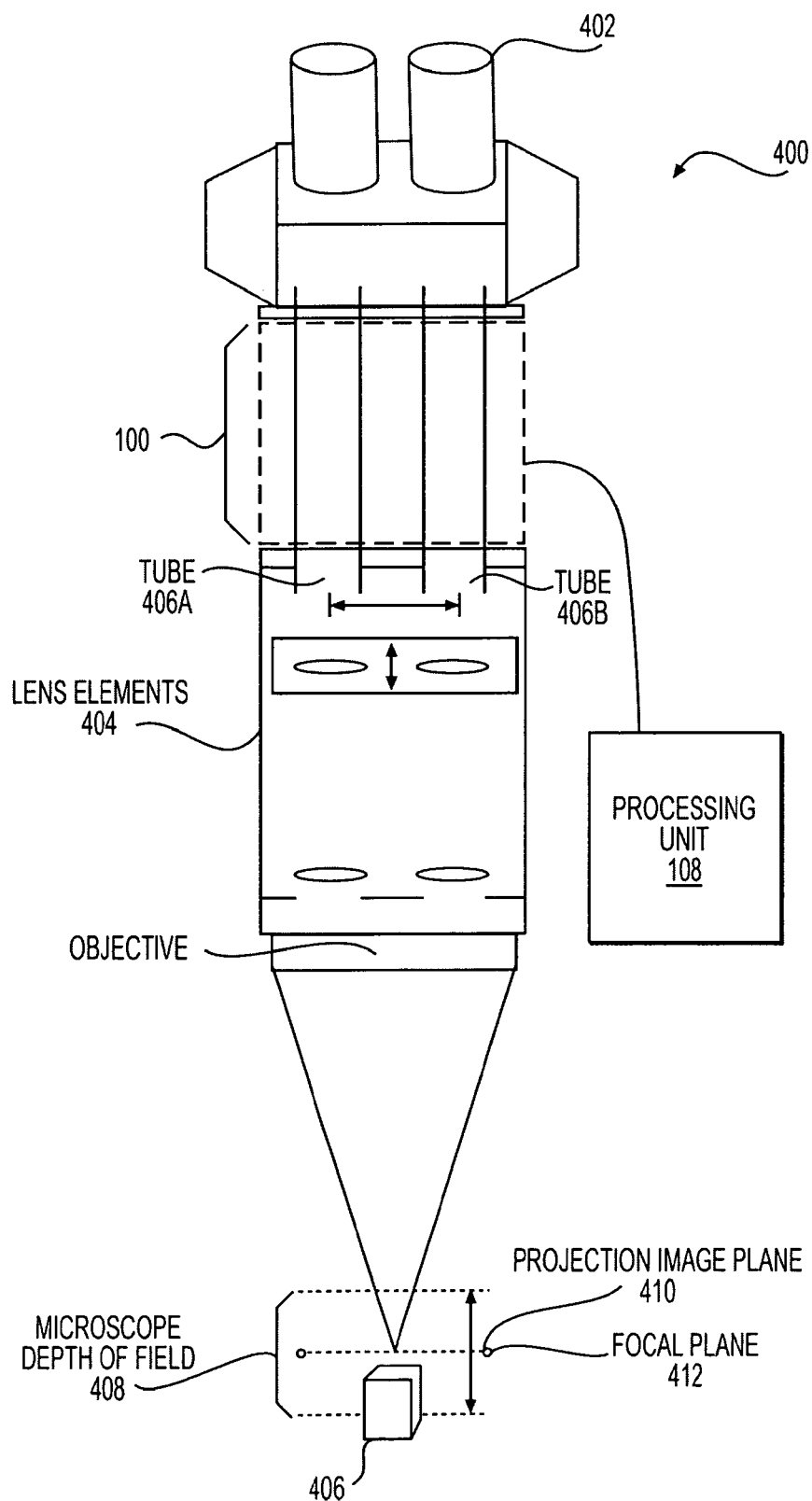
FIG. 4 illustrates a microscope system including an microscope insert according to an embodiment.
Figure 5:
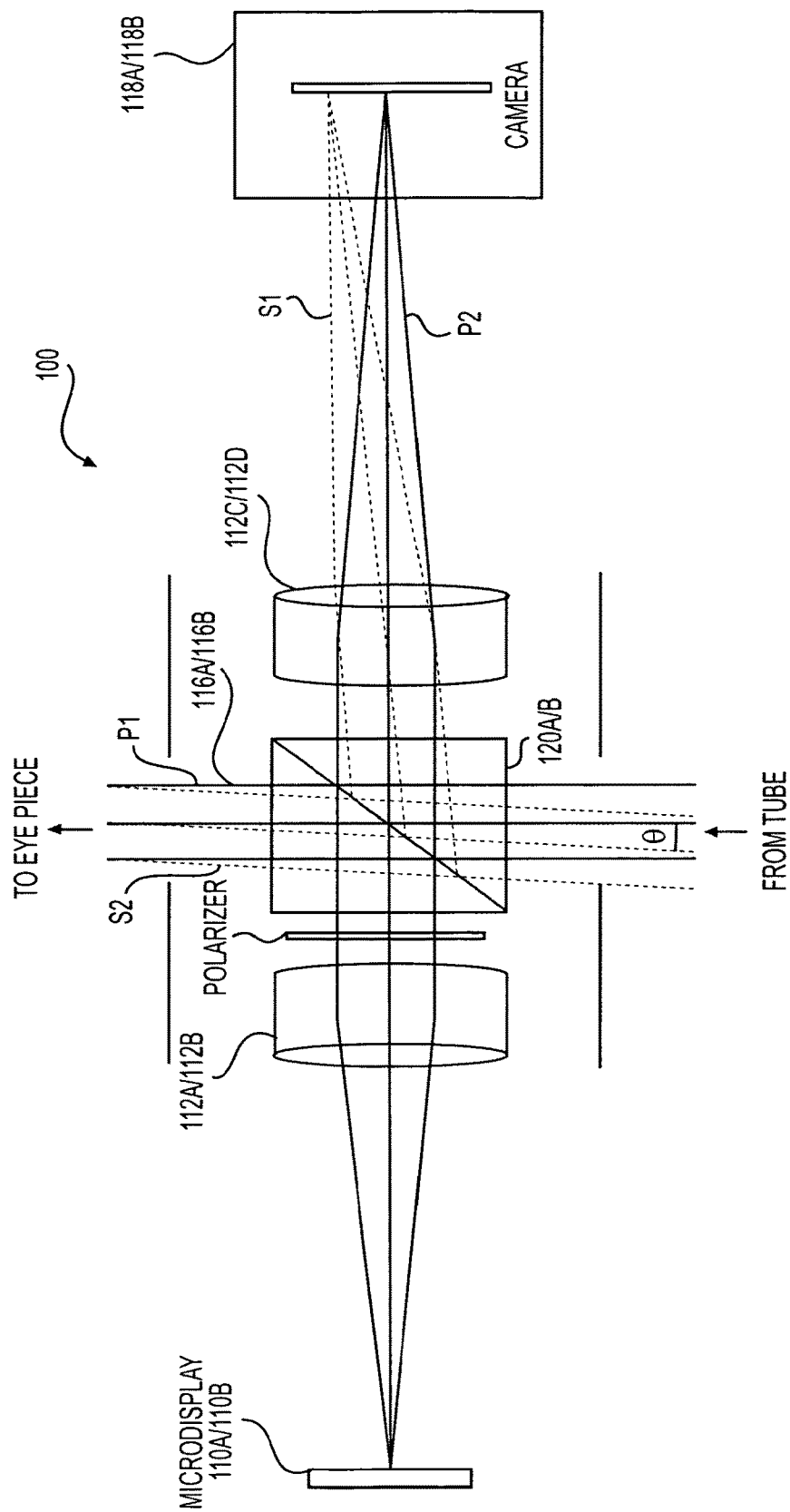
FIG. 5 illustrates light paths within a microscope insert according to an embodiment.

FIGS. 4 and 5 illustrate the operation of a microscope insert according to an embodiment using insert 100 as an example. As shown in FIG. 4, microscope insert 100 may be integrated with a microscope 400 that is suitable for various purposes. In an embodiment, microscope 400 may be a stereoscopic, infinity-corrected, tube microscope. Alternatively, microscope insert 100 may be adapted for use in other microscope layouts and stereoscopic devices known in the art.

Microscope 400 may include a viewing device 402 that allows a user to view images of an object 406 placed under the microscope. Viewing device 402 may be a heads-up device including one or more eye pieces, through which the images of the object are presented to the user. Microscope 400 further includes a set of lens elements 404 that receive light reflected from the object and form microscopic images of the object based on the reflected light. Lens elements 404 transmit the microscopic images of the object to tubes 406A and 406B of microscope 400. Tubes 406A and 406B form light transmission paths (i.e., light paths) that direct the microscopic image of the object toward viewing device 402. The microscopic image may be an analog image in an embodiment.

As further shown in FIGS. 4 and 5, when insert 100 is installed in microscope 400, the polarizing beam splitters 120A and 120B are disposed in the respective light paths between lens elements 404 and viewing device 402 of the microscope, intercepting light coming from respective tubes 406A and 406B. The beam splitters 120A and 120B may also be placed at other locations within the microscope as one of ordinary skill in the art will appreciate. As further described below, beam splitters 120A and 120B may serve two functions in insert 100. First, they may direct a first component of the light signals coming from the object to respective cameras 118A and 118B so that cameras 118A and 118B capture images of the object. Second, they may merge a second component of the light signals coming from the object that is passed through to viewing device 402 with light signals projected from the display devices 110A and 110B.

In particular, in an infinity-corrected tube microscope, for example, light rays passing through the tube are generally parallel, similar to those from a source infinitely far away. Beam splitter 120A/120B splits the light coming up from the object into two portions, directing a first portion (i.e., an S-polarized component S1) towards camera 118A/118B and a second portion (i.e, a P-polarized component P1) towards viewing device 402 of the microscope. Lens 112C/112D between beam splitter 120A/120B and camera 118A/118B is used to focus the S-polarized component S1 exiting beam splitter 120A/120B onto the imaging sensor of camera 118A/118B.

More particularly, polarizing beam splitter 120A/120B receives light signals representing a microscopic image of the object from lens elements 404 through tubes 406A and 406B. Each of polarizing beam splitters 120A and 120B splits incident light signals by allowing one polarized component S1 to reflect and the other polarized component P1 to pass through. The polarized component P1 that passes through beam splitter 120A/120B reaches viewing device 402 and provide the user with the microscopic image of the object for viewing.

The polarized component S1 is reflected by beam splitter 120A/120B toward respective camera 118A/118B through respective tube lens 112C/112D. Camera 118A/118B receives the polarized component S1 reflected from beam splitter 120A/120B and converts the optical signals to electronic image data corresponding to the microscopic image of the object. Camera 118A/118B may then transmit the electronic image data to processing unit 108 for further processing.

Beam splitter 120A/120B operates in a similar manner on the display device side. In particular, display device 110A/110B renders images under the control of the driver circuit and projects light signals corresponding to the images to beam splitter 120A/120B through lens 112A/112B. Lens 112A/112B between beam splitter 120A/120B and respective display device 110N/110B converts the light signals projected from display devices 110A/110B to parallel light rays to match the up-ward parallel light rays coming from tube 406A/406B. Beam splitter 120A/120B splits the incident light signals coming from display devices 110A/110B, reflecting the S-polarized component S2 of the incident light signals originating from display devices 110A/110B and passing through the P-polarized component P2 to camera 118A/118B.

At viewing device 402, the reflected S-polarized component S2 from display devices 110A/110B is then merged or combined with the P-polarized component P1 passed through beam splitter 120A/120B from tube 406A/406B. As a result, the images of the object provided by the P-polarized component P1 and the images from display device 110A/110B provided by the S-polarized component 82 may be simultaneously viewed by the user through viewing device 402. In other words, when viewed through viewing device 402, the images generated by display devices 110A/110B appear as overlaid images on the images of the object formed by lens element 404.

Polarizing element 114 placed between lens 112A/112B and beam splitter 120A/120B is configured to adjust the polarization of those projected parallel rays from lens 112A/112B so as to adjust the ratio of the light component (i.e., the S2 component) reflected by beam splitter 120A/120B to the light component (i.e., the P2 component) passed through to camera 118A/18B. Accordingly, the intensity of the S-polarized component S2 may be adjusted relatively to the intensity of the P-polarized component P2. In an embodiment, the intensity of the S-polarized component S2 may be substantial equal to the P-polarized component P2 so that the light signals projected from display devices 110A/110B are equally split by beam splitter 120A/120B.

Additionally, by adjusting the polarization imposed by polarizing element 114, the intensity of the S-polarized component S2 may also be adjusted relatively to the intensity of the P-polarized component P1. As a result, the images on the display device 110A/110B may be adjusted to be brighter or dimmer with respect to the images of the object when viewed through viewing device 402.

According to a further embodiment, when the P-polarized component P1 and the S-polarized component S2 are combined by beam splitter 120A/120B, the user of microscope 400 may view a combined image including the microscopic image of the object and the overlaid image generated by display device 110A/110B. The optical components of the microscope insert may be adjusted so that the overlaid image may appear at a projection image plane 410 that substantially overlaps the focal plane of microscope 400 and is located within the depth of field 408 of microscope 400.

The microscope insert for a stereoscopic microscope, as shown in FIGS. 1-5, includes a set of imaging and projection hardware for each of the right and left tubes of the microscope so as to generate stereoscopic images. As a result, the insert includes four lenses 112A-112D, lens 112C and 112D configured to focus the images of the object to left and right camera 118A and 118B, and lens 112A and 112B configured to project the images generated by left and right display devices 110A and 110B to beam splitters 120A and 120B. In order to maximize optical efficiency and reduce aberrations, these lenses may be incorporated in a lens set.

In alternative embodiments, the microscope insert may include additional optical components, such as mirrors, prisms, or lenses, in the optical paths between the beam splitters and the cameras or between the beam splitter and the display devices to modify the directions of the light rays. The modified light rays may allow the optical components of the insert to be more freely arranged or repositioned so as to fit into a desired mechanical or industrial form.

Figure 6A:
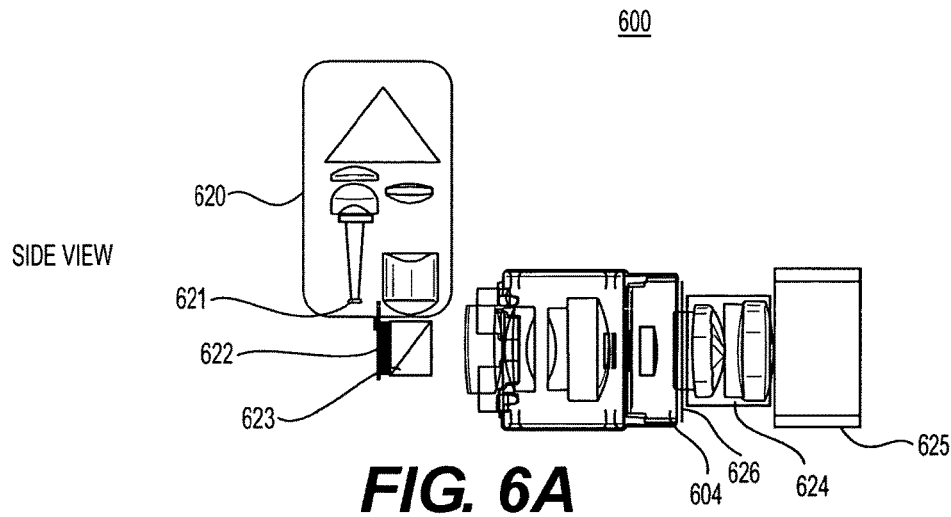
FIG. 6A illustrates a side view of various components assembled in a microscope insert according to an embodiment.
Figure 6B:
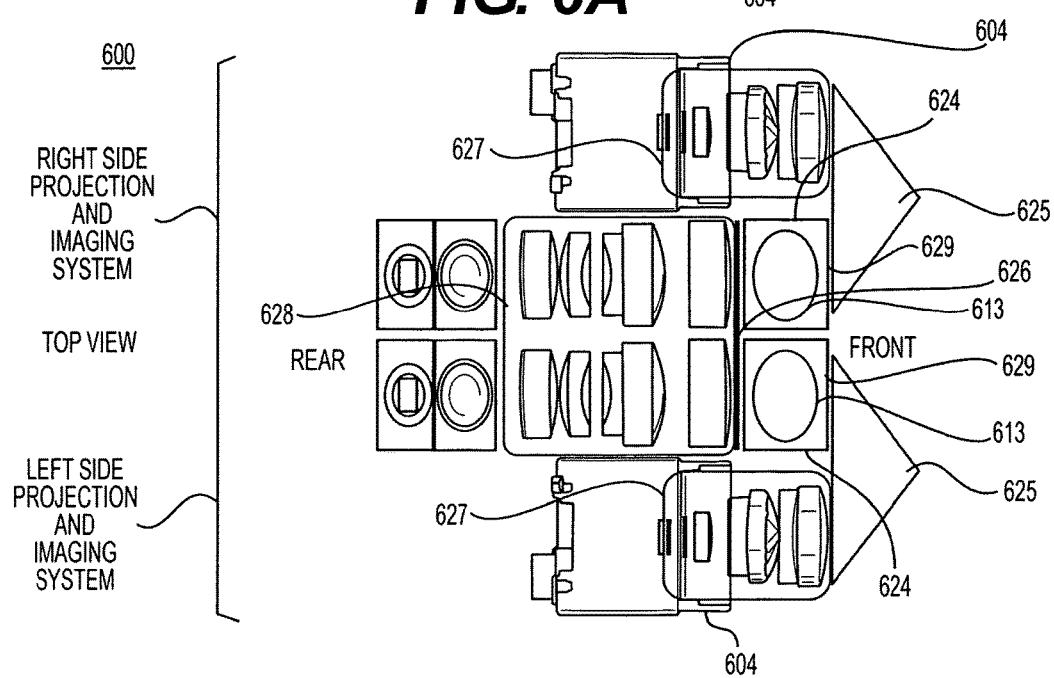
FIG. 6B is a top view of the various components assembled in the microscope insert according to an embodiment.

FIGS. 6A and 6B illustrate an embodiment of a microscope insert 600 including additional optical components to steer light rays. FIGS. 6A and 6B shows, respectively, a side view and a top view of major optical elements of microscope insert 600. Microscope insert 600 includes two optical channels for rendering images, respectively, for left and right eyes of the user. Although only one optical channel is described here, one of ordinary skill in the art will appreciate that the optical channels include similar elements and operate in similar manor.

Each optical channel of microscope insert 600 includes a polarizing beam splitter 624 disposed in the corresponding light pathway of the microscope and coupled to the tube of the microscope, from which light reflected by an object enters microscope insert 600. A portion (i.e., the S-polarized component S1) of the incident light is diverted to a turning prism 625, which directs the S1 component through imaging lenses 627 on to a camera 604.

The other portion (i.e., the P-polarized component P1) of the incident light passes through a polarizing beam splitter 624 and reaches the eyepiece of the microscope to provide a microscopic image of the object that is placed under the microscope. In an additional embodiment, beam splitter 624 may include a polarizer element configured to adjust the ratio of the light component diverted to camera 604 to the light component passed through to the eyepiece. The ratio may be, for example, 1:1, 1:2, 1:3, or other desired value.

The images generated by the processing unit and to be overlaid on the microscopic images of the object are rendered by a projection LCOS display panel 622 illuminated by an RGB LED light source 621. The S-polarized light component S2 of the light generated by LED light source 621 is passed through a set of display illumination optics 620 including illumination lenses and a turning prism. From illumination optics 620, the S-polarized light component S2 is reflected at the hypotenuse of a polarizing beam splitter 623 to LCOS display panel 622. LCOS display panel 622 acts as an active polarizer. The P-polarized light component P2 passes through a projection lens module 628 and a polarizing wave plate 626 to tube polarizing beam splitter 624. The P-polarized light component P2 is then directed to camera 604 by tube polarizing beam splitter 624 and steering prism 625. The S-polarized light component S2 is diverted and reflected by tube polarizing beam splitter 624 to the eyepiece of the microscope, which then visualizes the microscopic images of the object and the images generated by display panel 622. When viewed through the eyepiece, the images generated by display panel 622 are overlaid on the microscopic images of the object.

Alternatively, polarizing wave plate 626 may be omitted. Accordingly, the light from LCOS display panel 622 passes through tube polarizing beam splitter 624 without being reflected to the eye piece. Instead, the light from LCOS display panel 622 is directed to turning prism 625 and, in turn to, imaging lens 627 and camera 604. The benefit of this configuration is that wave plate 626 can be removed to perform a calibration between display panel 622 and camera 604. Based on calibration, the system may confirm that images generated by display panel 622 are aligned to the image space being measured by camera 604.

FIGS. 7A and 7B illustrate an embodiment of a microscope insert 700 that is similar to microscope insert 600 described above. The components of microscope insert 700 are packaged and assembled on a base plate 711 so that microscope insert 700 is ready to be installed on a microscope. In particular, insert 700 includes one or more optical channels, each including components similar to those of insert 600 illustrated in FIGS. 6A and 6B.

Each optical channel includes a camera 704 disposed in a camera housing affixed to base plate 711, a set of imaging lenses disposed in a lens tube 705, an imaging steering prism secured to base plate by prism bracket 706, a set of illumination optics disposed in an illumination optics housing 709, a set of projection lenses disposed in a lens tube 710. A focus mechanism is provided in imaging lens tube 705 and allows for fine adjustment of the relative position of the imaging lenses therein, for focusing. Likewise, a focus mechanism is also provided in display lens tube 710 and allows for fine adjustment of the position of the projection lenses for focusing.

Each optical channel further includes an RGB LED light source and a display panel mounted to base plate 711 through a display and RGB LED mounting bracket 714. Microscope insert 700 further includes a driver circuit board 707 mounted to base plate 711 through a driver board bracket 708.

Microscope insert 700 further includes mounting components for mounting onto a microscope. For example, insert 700 includes a top mount 701 that may be coupled to the eyepieces of the microscope. Top mount 701 may include features that allow the eyepieces to be secured thereon. Top mount 701 is secured to base plate 701 through one or more top mount braces. Top mount 701 includes one or more microscope tube openings that allow light to pass through from the polarizing beam splitters to the eye pieces of the microscope. Top mount 701 further includes a wave plate slot 712 for disposing and securing the wave plate. The wave plate may be easily inserted into wave plate slot or removed therefrom as desired. Microscope insert 700 further includes a bottom mount flange 702 that may be coupled and secured to the microscope tube within the body of the microscope.

Figure 8:
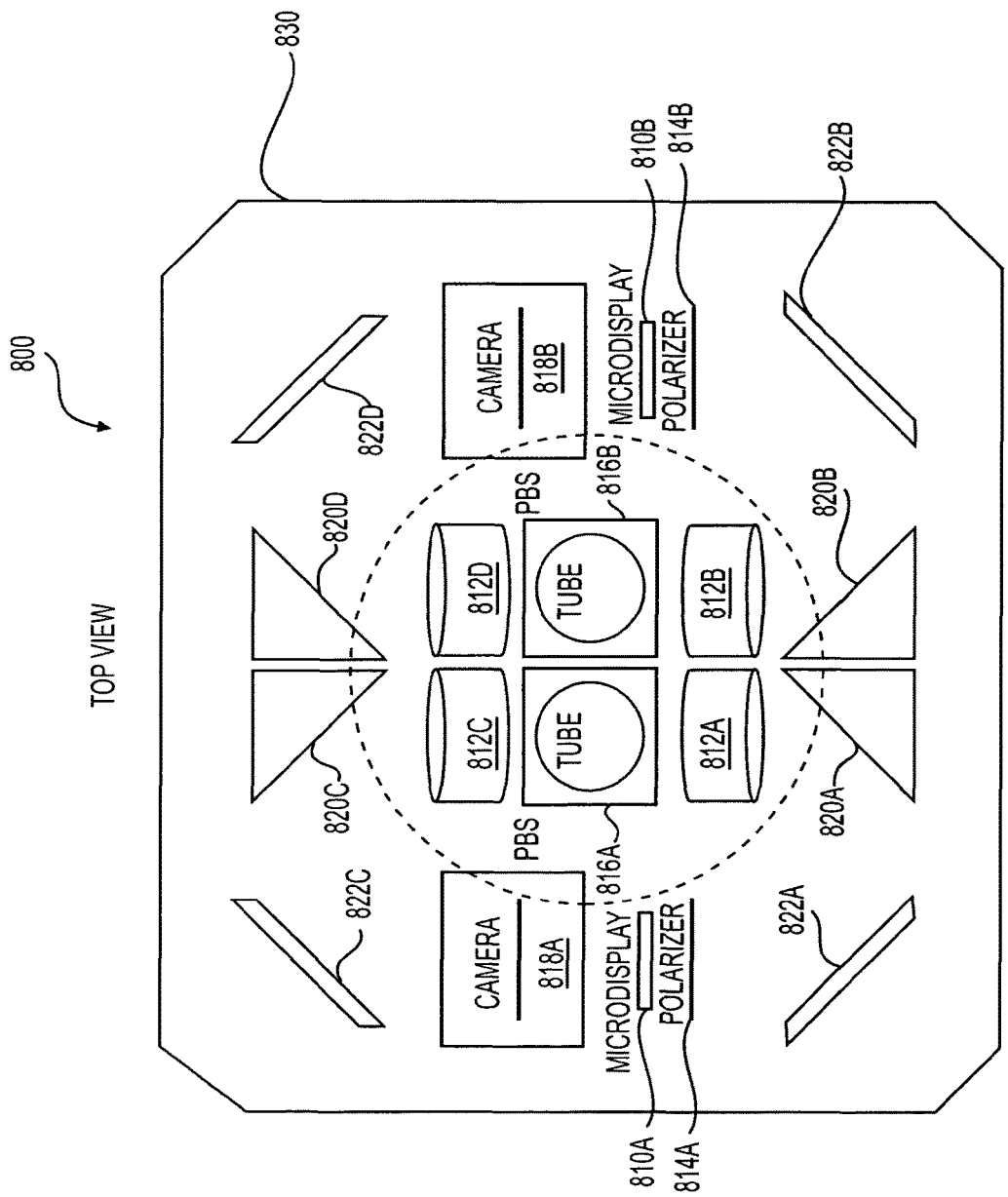
FIG. 8 is a schematic diagram of a microscope insert according to an embodiment.

FIG. 8 illustrates a microscope insert 800 according to another embodiment. In this embodiment, light reflected from the object under the microscope (not shown) is directed from the tubes (e.g., 406A and 406B of FIG. 4) to respective cameras 818A and 818B by a group of reflective mirrors and prisms 820C, 820D, 822C, and 822D. Similarly, the images generated by display devices 810A and 810B are projected back to beam splitters 816A and 816B by another group of mirrors and prisms 820A, 820B, 822A, and 822B. The arrangement in this embodiment allows the components to be disposed on a relatively small base plate that has a relatively small footprint, thereby easing integration in a variety of microscopic systems.

As further shown in FIG. 8, a polarizer element 814A/814B may be disposed in the light path between display device 810A/810B and beam splitter 816A/816B and is used to vary the amount of light passed through to camera 818A/818B from display device 810A/810B. Polarizing element 814A/814B may be a set of polarizers, wave plates, or variable retarders, depending on the output polarization of display devices 810A and 810B. In an embodiment, display device 810A/810B outputs an S-polarized component, which is then rotated by a ½-lambda wave plate in polarizing element 814A/814B so as to be reflected upwardly to the eyepiece for viewing by the user.

The microscope inserts disclosed herein may create a stereoscopic image. In particular, the inserts may create separate images for the left and right eyes of the user. The images are shifted with respect to each other to provide the perception of different convergence, resulting in stereoscopic rendering.

Figure 9:
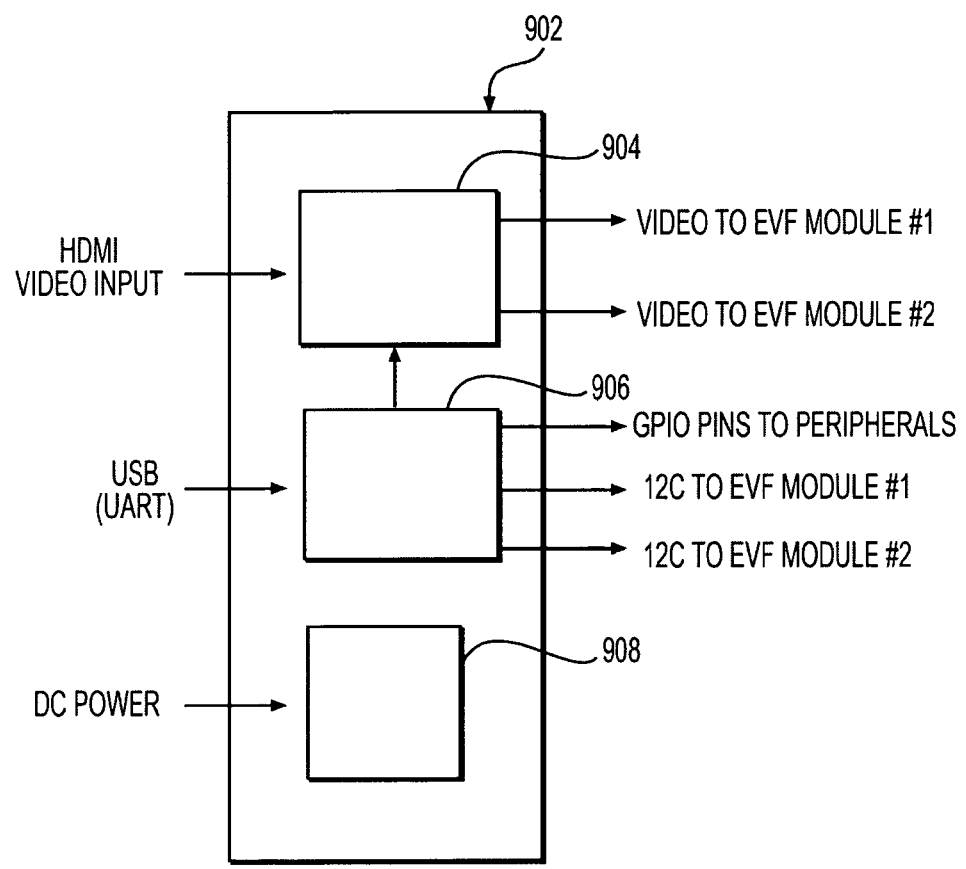
FIG. 9 is a schematic diagram of an insert driver circuit board for a microscope insert according to an embodiment.

FIG. 9 is a schematic diagram of a display driver circuit 900 according to an embodiment. Display driver circuit 900 generally corresponds to driver circuit 102 of FIG. 1. Driver circuit 900 provides communication interfaces between processing unit 108 and display devices 110A and 110B. The functions of driver circuit 900 may include, for example:

Communicating customized resolution HDMI video signals from processing unit 108 to display devices 110A and 110B;

Generating image frames of a desired resolution (i.e., 1976×960), including a side by side (SBS) layout of the left and right images to be displayed to the user;

Using line phasing to split the SBS image frames into left and right image signals;

Directing the image data to each display device 110A/110B; and

Providing a USB interface for communication with processing unit 108, which supports, for example, firmware updates, control of brightness, gamma, color channel gain of each display device, display focus, and status indication (i.e. power indication, insignia illumination, etc.).

According to an embodiment, processing unit 108 analyzes image data provided by cameras 118A and 118B and provides inputs to display driver circuit 102 for generating overlaid images through the display devices 110A and 110B. For example, processing unit 108 may analyze the image data for registration, tracking, or modeling the object under the microscope. Information derived from the analysis of the image data may then be used to generate and adjust the overlaid images generated by display devices 110A and 110B.

In a further embodiment, the microscope insert disclosed herein may be integrated in a microscope for ophthalmic procedures, such as cataract surgery. The microscope insert may generate images representing surgery-related information to assist a surgeon to navigate during a cataract surgery. The images may be displayed to the user overlaid with the real-time microscopic image of the patients eye. As a result, the surgeon is able to simultaneously view the image of the eye and the overlaid images through the microscope.

Figure 10:
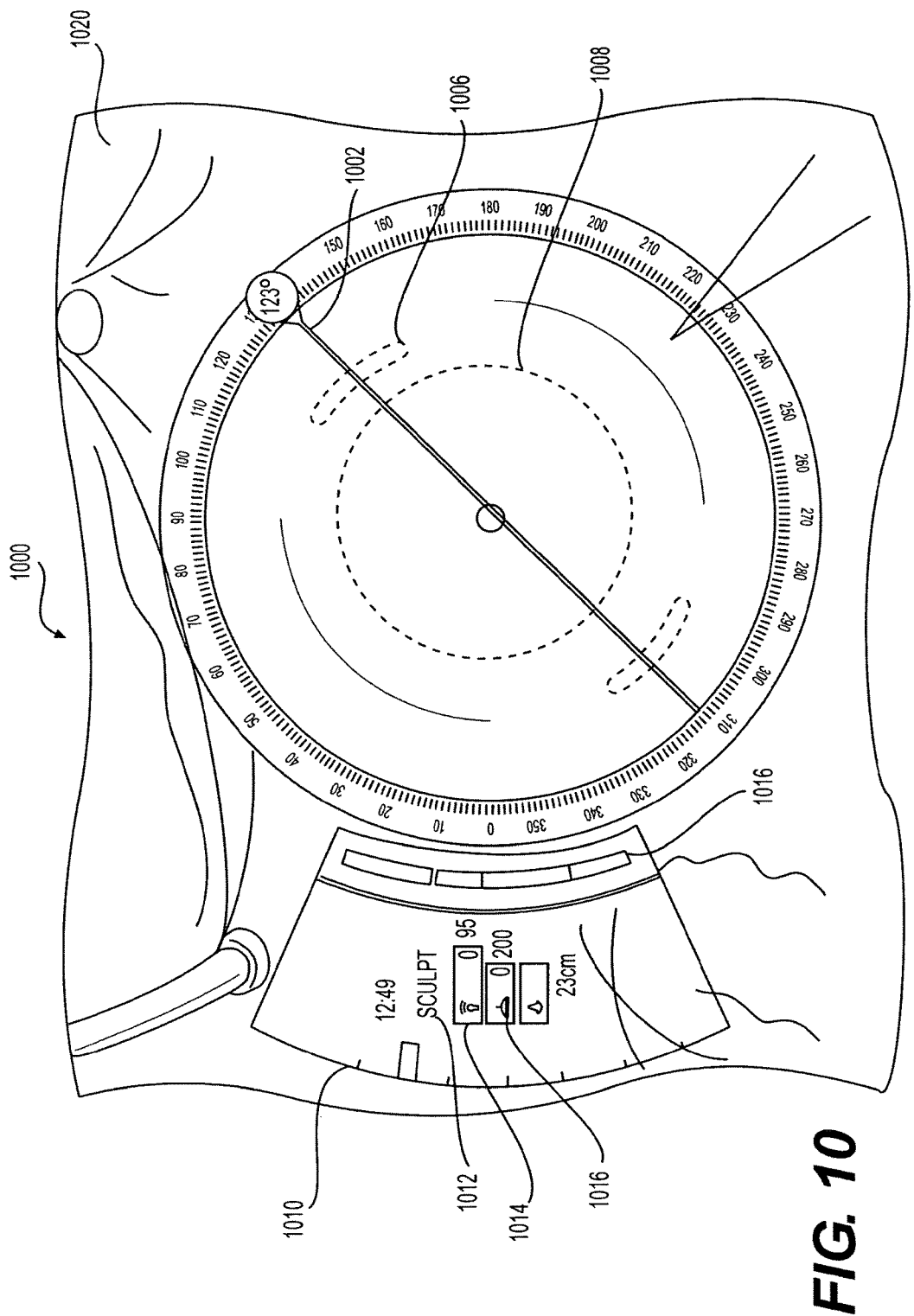
FIG. 10 illustrates graphical information generated by an microscope insert according to an embodiment.

FIG. 10 illustrates an exemplary composite image 1000 rendered by a microscope having a microscope insert described herein, according to an embodiment. Image 1000 includes a real-time microscopic image 1020 of a patient's eye as viewed through the microscope and images generated by the microscope insert overlaid on the real-time eye images. Microscopic image 1020 of the patient's eye may be an analog image formed by the zoom lens elements of the microscope. The overlaid images generated by the microscope insert include graphical representations of information related to the surgical procedure. The overlaid images may include prompts or instructions to guide the surgeon during the surgery.

For example, the overlaid images may include image features indicating an axis of interest 1002 and incision points 1006 and 1008 to guide the surgeon to carry out incision and placement of the artificial lens. The overlaid images may also present information including parameters related to the surgery, such as the current operation stage 1012, ultrasound power 1014, vacuum suction 1016, current time, and the like. The information may be presented in an image area 1010 near the area of operation. Image area 1010 may have a shape that generally conforms to the shape of the patient's eye. The processing unit of the microscope insert is configured to track and determine the position, size, and rotation of the patient's eye as it is viewed through the microscope and adjust the position, size, and orientation of the overlaid images accordingly so that the overlaid images remain registered with the patient's eye.

The microscope insert described here may also receive external data from external data sources and user inputs from user input devices during a surgical procedure, and adjust the overlaid images accordingly. For example, during a cataract surgery, the processing unit may receive, from the external data source, demographic information, bio-information, and medical history of the patient. The external data source may include a monitoring system that monitors status of surgical equipment or status of the patient, such as heart rate, respiratory rate, blood pressure, eye pressure, and the like, during the surgery. The processing unit may receive, from the monitoring system, the external data including real-time information representing the status of the patient and the equipment and presenting the external data as part of the overlaid image displayed to the operating surgeon through the microscope insert.

Additionally, the processing unit may receive user inputs from the surgeon through the input devices, such as a joy stick, a foot pedal, a keyboard, a mouse, etc. The user inputs may instruct the processing unit to adjust the information displayed in the overlaid images. For example, based on the user inputs, the processing unit may select portions of the external data for display as part of the overlaid images.

The processing unit may also display prompts or navigation instructions related to the surgical procedure according to the user inputs. For example, when the surgeon completes a step of a surgical procedure and presses the foot pedal, the processing unit may control microscope insert to modify the overlaid images so as to display prompts or instructions for the next step. The prompts or instructions may include text or graphical information indicating the next step and may further include data or parameters relevant to the next step.

The processing unit may also control the microscope insert to generate a warning to alert the surgeon if there are abnormalities during a surgical procedure. The warning may be a visual representation such as a warning sign generated by the display devices as part of the overlaid image. The warning may also be other visual, audio, or haptic feedback, such as a warning sound or a vibration.

Figure 11:
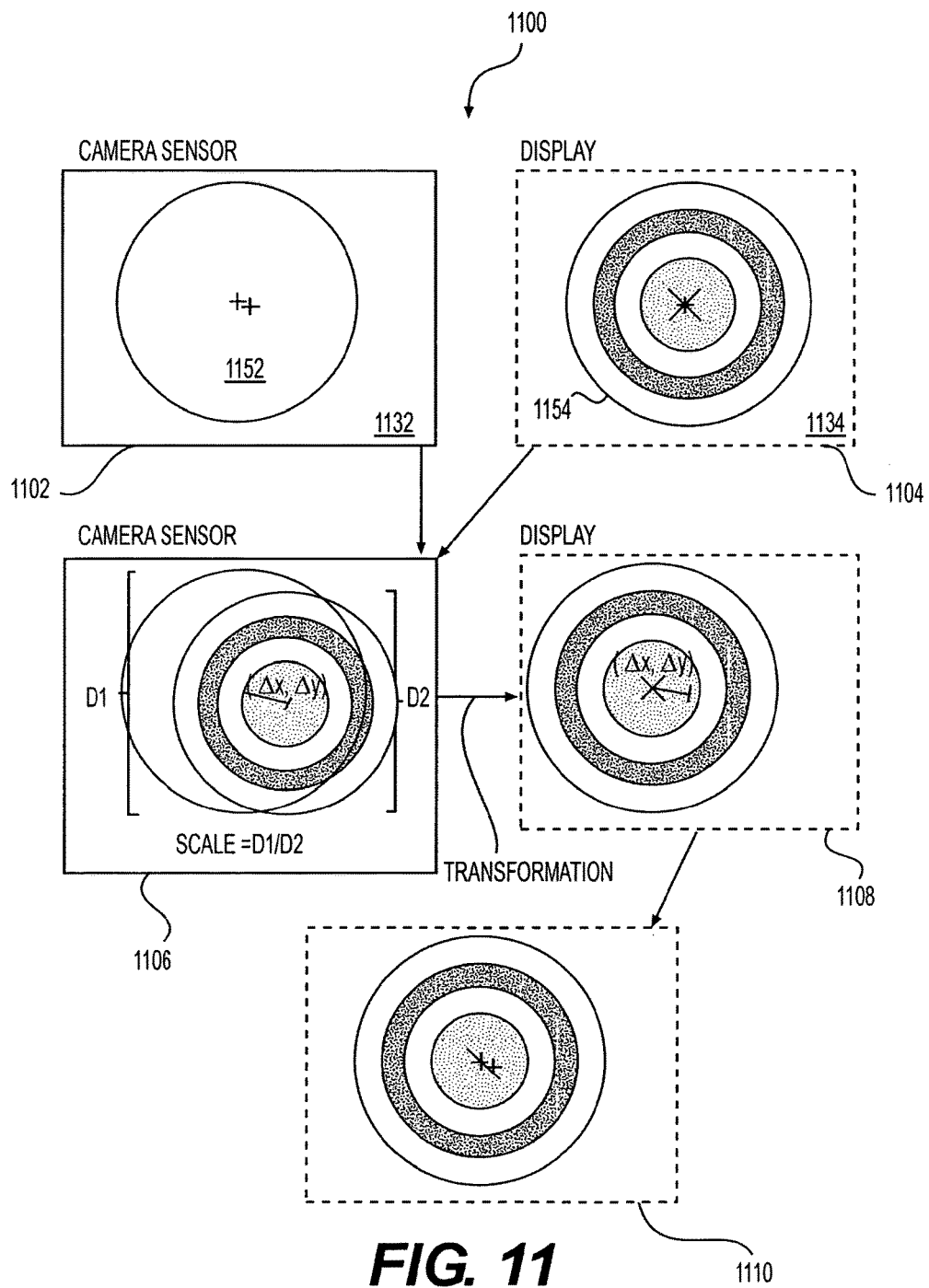
FIG. 11 illustrate a process for correcting a field of view of the microscope insert according to an embodiment.

During the operation of the microscope insert, the field of view provided by the display device of the insert may be different from the field of view of the microscope. FIG. 11 illustrates a process 1100 for correcting the field of view provided by the display devices and matching it with the field of view of the microscope.

According to process 1100, at step 1102, the microscope generates a microscopic image 1132 having a field of view 1152. At step 1104, the microscope insert generates an overlaid image 1134 having a field of view 1154. In an embodiment, fields of view 1152 and 154 may each have a circular shape. Field of view 1152 may have a diameter D1, and field of view 1154 may have a diameter D2.

At step 1106, overlaid image 1134 generated by the microscope insert and microscopic image 1132 generated by the microscope are displayed to the user through the eyepiece. When viewed through the eyepiece, microscopic image 1132 and overlaid image 1134 are combined or overlaid. However, due to mismatch between the fields of view of the two images, image features of overlaid image 1134 may obscure important image features of microscopic image 1132 or may appear to be disproportional to the image features of microscopic image 1132.

In order to align the fields of view of the two images, overlaid image 1134 must be adjusted according to the field of view of microscopic image 1132. As discussed above with reference to FIG. 5, polarization imposed by polarizing element 114 on light signals projected by display device 110A/110B allows a portion (i.e., the P-polarized component P2) of the light signals to pass through polarizing beam splitter 120A/120B. The passed-through light from display device 110A/110B is received by camera 118A/118B, which captures overlaid image 1134. On the other hand, camera 118A/118B receives light (i.e., the S-polarized component S1) from the object, which is reflected by beam splitter 120A/120B, and captures microscopic image 1132 generated by the microscope. The processing unit (i.e., processing unit 108 of FIG. 1) then compare overlaid image 1134 with microscopic image 1132 to determine image transformations necessary to match field of view 1154 of overlaid image 1134 with field of view 1152 of microscopic image 1132.

At step 1108, the processing unit then applies the image transformations to overlaid image 1134 generated by the display device and control the display device to generate an adjusted overlaid image 1138. As a result, the field of view provided by the display device is properly aligned with the field of view of the microscope at step 1110.

Process 1100 may be used to correct any optical misalignment during manufacturing or slight damages from handling. The image transformations used by the processing unit may be affine transformations. Typical transformations may include translation, scaling, skewing, rotation, and the like. For example, the processor unit may determine a scaling factor for scaling overlaid image 1134 based on a ratio between the diameter D1 of field of view 1152 and the diameter D2 of field of view 1154. The processor unit may also determine translation parameters (Δx and Δy) necessary to align the microscopic image and the overlaid image based on the distance between the circular centers of fields of view 1152 and 1154. Using process 1100, the microscope insert may provide more precisely placed overlaid images over the microscopic images when viewed through the eyepiece of the microscope.

According to additional embodiments, the processing unit may monitor changes in the field of view of the microscopic image (i.e., based on the S-polarized component S1) during operation and adjust the overlaid image in such a way to track or follow the field of view of the microscopic image. Alternatively, the processing unit may track an anatomical feature of the patient under the microscope and adjust the field of view of the overlaid image to follow the anatomical feature.

According to another embodiment, the camera (i.e., camera 118A/118B of FIG. 1) is configured such that field of view 1152 of the microscope is entirely captured by the camera sensor. Similarly, the overlaid image generated by the display device (i.e., display device 110A/110B) is configured to cover entirely field of view 1152 of the microscope. The camera sensor and the display device are configured to provide oversampling so as to provide sufficient resolutions over the image area that covers the field of view of the microscope.

Figure 12:
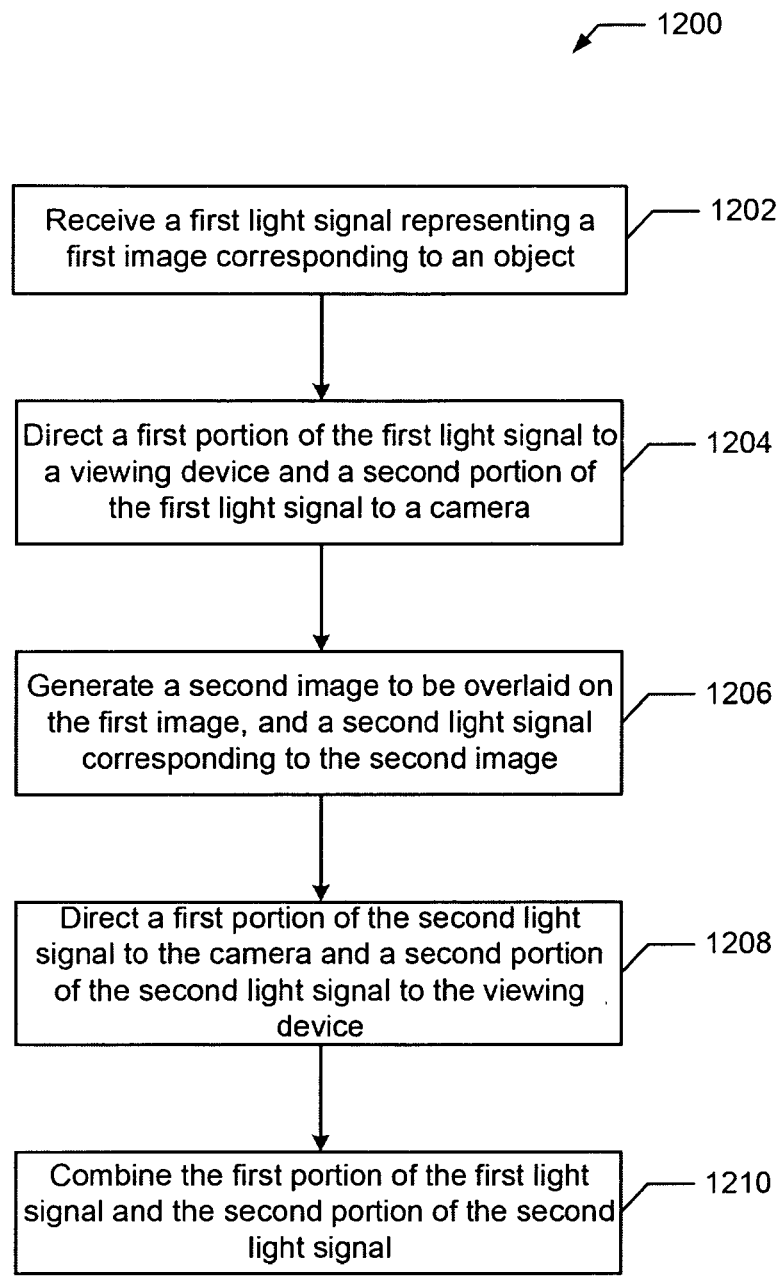
FIG. 12 illustrates a process for generating an overlaid image in a microscope according to an embodiment.

FIG. 12 illustrates a process 1200 for generating an overlaid image over a microscopic image, according to an embodiment. Process 1200 may be implemented on the microscope insert (i.e., microscope insert 100) disclosed herein.

According to process 1200, at step 1202, the microscope insert receives a first light signal from a microscope (i.e., microscope 400). The first light signal represents a first image corresponding to an object (i.e., object 406) placed under the microscope. As shown in FIGS. 4 and 5, the first light signal may be received from the zoom lens elements of the microscope through the tube within the body of the microscope. The first image may be an analog microscopic image of the object.

At step 1204, the microscope insert directs a first portion (i.e., the P-polarized component P1) of the first light signal to a viewing device (i.e., viewing device 402) and a second portion (i.e., the S-polarized component S1) of the first light signal to a camera (i.e., camera 118A/118B). More particularly, the first light signal may be split by the polarizing beam splitter (i.e., PBS 120A/120B) of the microscope insert into the first portion and the second portion. The polarizing beam splitter may be configured to allow the first portion of the first light signal to pass through to the viewing device and reflect the second portion of the first light signal to the camera within the microscope insert. The microscope insert may further include a tube lens (i.e., lens 112C/112D) to focus the second portion of the first light signal onto the camera sensor and/or additional light steering components (i.e., mirrors and prisms) to direct or redirect the second portion of the first light signal to the location of the camera.

At step 1206, a display device (i.e., display device 110A/110B) of the microscope insert generates a second image to be overlaid on the first image. The second image (i.e., the overlaid image) includes graphical representations indicating information relevant to the object. For example, when the object is a patient's eye and a surgical procedure (i.e., a cataract surgery) is carried out on the object, the second image may include, for example, prompts, instructions, parameters, and data relevant to the underlying surgical procedure. By displaying the second image, the display device produces a second light signal representing the second image.

At step 1208, the microscope insert directs a first portion (i.e., the P-polarized component P2) of the second light signal to the camera and a second portion (i.e., the S-polarized component S2) of the second light signal to the viewing device. The second light signal may be split again by the polarizing beam splitter into the first portion and the second portion. The polarizing beam splitter may allow the first portion to pass through to the camera and reflect the second portion to the viewing device. The microscope insert may further include a tube lens (i.e., lens 112A/112B) between the display device and the polarizing beam splitter to alter (i.e., expand) the second light signal projected by the display device. The microscope insert may also include additional light steering components (i.e., mirrors and prisms) to direct the second light signal from the display device to the location of the polarizing beam splitter. The microscope insert may also include a polarizer element (i.e., polarizer element 114) between the display device and the polarizing beam splitter. The polarizer element may impose polarization on the second light signal so as to adjust the ratio between the first portion of the second light signal, which is passed through to the camera, and the second portion of the second light signal, which is reflected to the viewing device.

At step 1210, the first portion of the first light signal and the second portion of the second light signal are combined to form a composite image, including the first image corresponding to the object and the second image generated by the display device. The second image, when viewed through the viewing device, is rendered over the first image. As a result, the user of the microscope (i.e., the surgeon) may simultaneously view the first image (i.e., the microscopic image of the patient's eye) and the second image (i.e., the overlaid image) through the viewing device (i.e., the eyepiece) of the microscope.

Additionally, at step 1210, the microscope insert may detect any mismatch between a field of the view of the first image and a field of view of the second image. The microscope insert may detect the mismatch based on the second portion of the first light signal and the first portion of the second light signal received by the camera. If there is a mismatch, the microscope insert may adjust the second image according to the image transformations described herein so as to match the field of view of the second image with the field of view of the first image.

This disclosure is not limited to the particular implementations listed above. Other display techniques, protocols, formats, and signals may also be used without deviating from the principle of this disclosure. Other embodiments of the invention will be apparent to those skilled in the art from consideration of the specification and practice of the invention disclosed herein. Although the microscope insert is described above in the context of a cataract surgery, one of ordinary skill in the art will appreciate that the microscope insert may be integrated in other surgical systems configured to carry out a variety of surgical procedures, such as spinal surgery, ear, nose, and throat (ENT) surgery, neurosurgery, plastic and reconstructive surgery, gynecological or oncological surgery, etc. For these procedures, the insert may be used for registration, tracking, and image recognition and to generate customized stereoscopic overlaid information relevant to the procedure and a particular patient's anatomy that is not limited to what is disclosed herein. It is intended that the specification and examples be considered as exemplary only, with a true scope and spirit of the invention being indicated by the following claims.

What is claimed:

1. A microscope insert, comprising:
a beam splitter configured to receive first light from an object, the beam splitter directing a first portion of the first light in a first direction to a viewing device and directing a second portion of the first light in a second direction;
a camera configured to receive the second portion of the first light from the beam splitter and to generate a first signal representing the object;
a processing unit configured to receive the first signal representing the object and determine characteristics of the object by analyzing the first signal, the processing unit further generating a second signal representing information relevant to the object;
a display device configured to receive the second signal from the processing unit and generate a graphical representation of the information based on the second signal, the display device transmitting second light corresponding to the graphical representation; and
a polarizer element configured to modify a polarization of the second light from the display device;
wherein:
the beam splitter receives the modified second light from the polarizer element and directs a first portion of the modified second light in the first direction to the viewing device; and
the first portion of the modified second light and the first portion of the first light from the object are combined for simultaneous viewing of the graphical representation and the object by the user.

2. The microscope insert of claim 1, further comprising:
a first lens disposed between the beam splitter and the camera for directing the second portion of the first light from the object to the camera; and
a second lens disposed between the beam splitter and the display device for converting the second light from the display device to substantially parallel rays of light.

3. The microscope insert of claim 1, wherein:
the beam splitter is further configured to direct a second portion of the modified second light in the second direction to the camera, and
the camera generates, based on the second portion of the modified second light, a third signal representing the graphical representation generated by the display device.

4. The microscope insert of claim 3, wherein:
the processing unit is further configured to:
determine a field of view based on the first signal from the camera;
compare the third signal and the first signal; and
adjust the graphical representation generated by the display device based on the comparison.

5. The microscope insert of claim 3, wherein the polarizer element is configured to adjust the polarization of the second light from the display device so as to adjust a ratio between the first portion of the modified second light and the second portion of the modified second light.

6. The microscope insert of claim 3, further comprising one or more light steering elements for directing the second portion of the modified second light to the camera.

7. The microscope insert of claim 6, wherein the one or more light steering elements comprise at least one of a mirror or a prism.

8. The microscope insert of claim 1, further comprising one or more light steering elements for directing the second portion of the first light from the object to the camera.

9. The microscope insert of claim 8, wherein the one or more light steering elements comprise at least one of a mirror or a prism.

10. The microscope insert of claim 1, further comprising a driver circuit configured to receive image data and control signals from the processing unit and coupled to the display device for controlling the display device according to the image data and the control signals.

11. The microscope insert of claim 1, further comprising a base plate for mounting one or more of the beam splitter, the camera, the processing unit, the display device, and the driver circuit.

12. The microscope insert of claim 11, wherein the base plate comprises a first mounting interface for mounting the microscope insert to a microscope such that the beam splitter intercepts a light path of the microscope.

13. The microscope insert of claim 12, wherein the beam splitter receives the light from the object through a set of lens elements of the microscope.

14. The microscope insert of claim 12, further comprising a second mounting interface for mounting the viewing device to the microscope insert.

15. The microscope insert of claim 1, wherein the first direction and the second direction are substantially perpendicular.

16. The microscope insert of claim 1, wherein the first portion and the second portion of the first light from the object have different polarization.

* * * * *